(12) United States Patent
Kersten et al.

(10) Patent No.: US 9,339,210 B2
(45) Date of Patent: May 17, 2016

(54) DEVICE FOR OBTAINING A VITAL SIGN OF A SUBJECT

(71) Applicant: KONINKLIJKE PHILIPS N.V., Eindhoven (NL)

(72) Inventors: Gerrit Maria Kersten, Veldhoven (NL); Ihor Olehovych Kirenko, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 92 days.

(21) Appl. No.: 14/258,085

(22) Filed: Apr. 22, 2014

(65) Prior Publication Data

US 2014/0334697 A1    Nov. 13, 2014

Related U.S. Application Data

(60) Provisional application No. 61/820,755, filed on May 8, 2013.

(30) Foreign Application Priority Data

May 8, 2013 (EP) .................................. 13167047

(51) Int. Cl.
*G06K 9/00* (2006.01)
*A61B 5/08* (2006.01)
(Continued)

(52) U.S. Cl.
CPC ........... *A61B 5/0816* (2013.01); *A61B 5/02416* (2013.01); *A61B 5/1128* (2013.01);
(Continued)

(58) Field of Classification Search
CPC .. A61B 5/0816; A61B 5/7271; A61B 5/0077; A61B 5/02416; A61B 5/1128; A61B 5/113; G06T 2207/10016; G06T 2207/20068; G06T 2207/30076; G06T 7/2053; G06T 7/20; G06K 9/0051
USPC ......................................................... 382/128
See application file for complete search history.

(56) References Cited

U.S. PATENT DOCUMENTS 5,734,739 A * 3/1998 Sheehan ............... G06T 7/0012
382/128
6,110,123 A 8/2000 Ishihara et al.
(Continued)

FOREIGN PATENT DOCUMENTS

CN   103054569 B * 4/2015 ........... A61B 5/0245
EP   2417908 A1   2/2012
(Continued)

OTHER PUBLICATIONS

Van Den Helder, M.; Motion Robust Techniques for Camera-based Monitoring of Respiration; 2011; Technical University Eindhoven; 11 pages.

*Primary Examiner* — Gregory F Cunningham (57) ABSTRACT

A device for obtaining a vital sign of a subject despite motion of the subject, in particular for discriminating a vital sign such as a respiratory information signal from noise in a projection based vital signs registration, comprises an interface that receives a set of image frames of a subject. An analysis unit determines the amount of direction changes and/or the time distances between direction changes within a region of interest in a subset of image frames comprising a number of image frames of said set. An evaluation unit determines if said region of interest within said subset of image frames comprises a vital sign information and/or noise by use of the determined amount of direction changes and/or the time distances for said subset of image frames. A processor determines the desired vital sign of the subject from said region of interest within said subset of image frames.

16 Claims, 8 Drawing Sheets

(51) Int. Cl.
*A61B 5/00* (2006.01)
*A61B 5/024* (2006.01)
*A61B 5/11* (2006.01)
*G06T 7/20* (2006.01)
*A61B 5/113* (2006.01)

(52) U.S. Cl.
CPC ............ *A61B5/7271* (2013.01); *G06K 9/0051* (2013.01); *G06T 7/2053* (2013.01); *A61B 5/0077* (2013.01); *A61B 5/113* (2013.01); *G06T 2207/10016* (2013.01); *G06T 2207/20068* (2013.01); *G06T 2207/30076* (2013.01)

(56) References Cited

U.S. PATENT DOCUMENTS

| | | | |
|---|---|---|---|
| 7,431,700 B2 | 10/2008 | Aoki et al. | |
| 2008/0285819 A1* | 11/2008 | Konofagou | A61B 8/08 382/128 |
| 2010/0130873 A1 | 5/2010 | Yuen et al. | |
| 2010/0152600 A1 | 6/2010 | Droitcour et al. | |
| 2011/0317874 A1* | 12/2011 | Ikenoue | G06F 3/017 382/103 |
| 2013/0135137 A1 | 5/2013 | Mulder et al. | |
| 2013/0271591 A1 | 10/2013 | Van Leest et al. | |
| 2013/0345585 A1 | 12/2013 | Gopal Samy et al. | |
| 2014/0019631 A1* | 1/2014 | Namboodiri | H04L 65/60 709/231 |
| 2014/0088433 A1 | 3/2014 | Shan et al. | |
| 2014/0135625 A1* | 5/2014 | Konofagou | A61B 8/0883 600/443 |

FOREIGN PATENT DOCUMENTS

| | | | |
|---|---|---|---|
| WO | 2012093358 A1 | 7/2012 | |
| WO | 2012123828 A1 | 9/2012 | |
| WO | 2012140531 A1 | 10/2012 | |
| WO | WO 2014024104 A1 * | 2/2014 | ............ A61B 5/08 |

\* cited by examiner

DEVICE FOR OBTAINING A VITAL SIGN OF A SUBJECT

CROSS REFERENCE TO RELATED APPLICATIONS

This application claims the benefit of U.S. provisional application Ser. No. 61/820,755 filed May 8, 2013, and European provisional application serial no. 13167047.3 filed May 8, 2013, both of which are incorporated herein by reference.

FIELD OF THE INVENTION

The present invention relates to a device, method and system for obtaining a vital sign, in particular a respiratory information, of a subject. In particular, the present invention relates to an unobtrusive optical measurement approach which can be used for detecting vital signs in an observed subject, such as a person or animal.

BACKGROUND OF THE INVENTION

Vital signs of a person, for example the heart rate, the respiration rate or the blood oxygen saturation, serve as indicators of the current state of a person and as powerful predictors of serious medical events. For this reason, vital signs are extensively monitored in inpatient and outpatient care settings, at home or in further health, leisure and fitness settings.

WO 2012/140531 A1 discloses a respiratory motion detection apparatus for detecting the respiratory motion of a person. This detection apparatus detects electromagnetic radiation emitted and/or reflected by a person wherein this electromagnetic radiation comprises a continuous or discrete characteristic motion signal related to the respiratory rate of the person and other motion artifacts related to the movement of the person or related to ambient conditions. This apparatus increases the reliability of the respiratory rate measurement by taking into account data processing means adapted to separate the respiratory rate signal from overall disturbances by taking into account a predefined frequency band, common predefined direction or an expected amplitude band and/or amplitude profile to distinguish the different signals.

Non-invasive respiratory rate measurements can be accomplished optically by use of a stationary video camera. A video camera captures the breathing movements of a patient's chest in a stream of images. The breathing movements lead to a temporal modulation of certain image features, wherein the frequency of the modulation corresponds to the respiratory rate of the patient monitored. Examples of such image features are the average amplitude in a spatial region of interest located around the patient's chest, or the location of the maximum of the spatial cross correlation of the region of interest in subsequent images. The quality and the reliability of the obtained vital sign information are largely influenced by the quality of the input image data influenced by an appropriate selection of the image contrast and the selected region of interest.

Camera-based respiration monitoring is based on detecting subtle respiration motion in the selected region of interest (ROI) in the chest/belly area. In real-life use scenarios, a static noise present in an image (including ROI) can be registered, amplified and (falsely) recognized as a respiratory signal. This might happen in cases when only the ROI is analyzed, as well as when a whole image is divided into spatial blocks, which are analyzed separately. Certainly, the noise might be registered as respiratory signal, if a final reconstructed signal is used to evaluate its validity, because in this case a differentiation of noise from breathing is done based on an amplitude and/or frequency of the final 1D signal.

US 2010/130873 A1 discloses a radar-based physiological motion sensor. Doppler-shifted signals can be extracted from the signals received by the sensor. The Doppler-shifted signals can be digitized and processed subsequently to extract information related to the cardiopulmonary motion in one or more subjects. The information can include respiratory rates, heart rates, waveforms due to respiratory and cardiac activity, direction of arrival, abnormal or paradoxical breathing, etc. In various embodiments, the extracted information can be displayed on a display.

SUMMARY OF THE INVENTION

It is an object of the present invention to provide a device, method and system for obtaining respiratory information of a subject in a simple and low cost manner, in particular enabling to discriminate a respiratory signal from noise in a projection based vital signs registration.

In a first aspect of the present invention a device for obtaining vital sign of a subject is presented that comprises
an interface that receives a set of image frames of a subject,
an analysis unit that determines the amount of direction changes and/or the time distances between direction changes within a region of interest in a subset of image frames comprising a number of image frames of said set, a direction change indicating a change of the direction of motion appearing within said region of interest,
an evaluation unit that determines if said region of interest within said subset of image frames comprises a vital sign information and/or noise by use of the determined amount of direction changes and/or the time distances for said subset of image frames, and
a processor that determines the desired vital sign of the subject from said region of interest within said subset of image frames if it is determined that said region of interest within said subset of image frames comprises a vital sign information.

In a second aspect of the present invention a method for obtaining vital sign of a subject is presented that comprises
receiving a set of image frames of a subject,
determining the amount of direction changes and/or the time distances between direction changes within a region of interest in a subset of image frames comprising a number of image frames of said set, a direction change indicating a change of the direction of motion appearing within said region of interest,
determining if said region of interest within said subset of image frames comprises a vital sign information and/or noise by use of the determined amount of direction changes and/or the time distances for said subset of image frames, and
determining the desired vital sign of the subject from said region of interest within said subset of image frames if it is determined that said region of interest within said subset of image frames comprises a vital sign information.

In further aspects of the present invention a system for obtaining vital sign of a subject are presented, said system comprising an imaging unit for obtaining a set of image frames of a subject, and a device as disclosed herein for obtaining a vital sign of the subject by use of said set of images frames of the subject.

In yet further aspects of the present invention, there are provided a computer program which comprises program code means for causing a computer to perform the steps of the processing method when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

The above described problem could be solved by analysing motion vectors per each block of pixels of the region of interest. For instance, a consistent motion field generated by adjacent spatial blocks would indicate that the detected signal represents a respiratory motion. However, this approach is very expensive (requires an accurate motion estimation), requires careful tuning of parameters for analysing motion vectors, and still does not solve the problem for all cases (e.g. shallow breathing might be not recognisable by motion estimation). Other possible solutions could rely on frequency analysis to differentiate a non-periodic noise signal from respiration. However, the breathing signal is often non-periodic as well. Moreover, due to low rate on respiratory signal, frequency analysis might require a very large temporal window.

The present invention provides a simple, low cost device and method to robustly discriminate a vital sign, in particular a shallow respiratory signal, from noise in a vital signs registration using a set of image frames obtained e.g. from a camera. The present invention is based on the idea to focus on the raw input values (i.e. the image frames) that are used to build the reconstructed signal (i.e. a vital sign information signal or the vital sign obtained from the vital sign information signal) rather than on the reconstructed signal and observes the amount of direction changes and/or the time distances between direction changes within a region of interest measured per unit of time (i.e. in a subset of image frames comprises a predetermined or varying number of subsequent image frames) to discriminate between a vital sign information and noise. It is particularly decided if from the image frames of the subset a vital sign can be retrieved, preferably if there is a sufficiently large signal-to-noise ratio to derive the vital sign with a desired accuracy and reliability, or if the used image frames mainly comprise noise. The invention is based on the observation of these raw input values, which revealed that the number of direction changes (or sign changes) in a (noisy) static scene is much higher and/or the time distances between direction changes are lower than when the scene contains breathing motion.

According to an embodiment said evaluation unit is configured to determine if the determined amount of direction changes is lower than a predetermined direction change threshold indicating that said region of interest within said subset of image frames comprises a vital sign information. Said direction change threshold may be predetermined or changeable, e.g. adaptable according to the frame rate within the subset or settable by the user. A direction change generally applies to the (change in) direction of the correlation peak between two subsequent image frames. A direction change may also be detected by detecting zero crossings within a projection, as will be explained below. After changes of the direction, a projection crosses the zero axis so that a zero crossing can be used as an indicator for a direction change.

According to another embodiment a projection based approach is provided according to which said analysis unit is configured to determine a projection profile in a predetermined direction from said subset of image frames and for determining said amount of direction changes from said projection profile. A projection based respiratory monitoring is described in the above mentioned WO 2012/140531 A1. The concept of generating a projection and a projection profile (a collection of projection profiles being called motion profile herein; the final 1D signal can be reconstructed from the motion profile) as described in WO 2012/140531 A1 are evaluated herein. The final 1D signal can be reconstructed from the "motion profile Related explanations of WO 2012/140531 A1 are thus herein incorporated by reference.

Generally, a profile is a one-dimensional representation of an image frame obtained through a projection-like transformation. In a broader sense, the profile can be any function that captures information about texture, edges, or any other detail present in the image frame. In its simplest form, profile can be the same as a projection (accumulation of pixel values in one direction); in a broader sense, a profile can be a product of projection and other function of pixels (e.g. standard deviation). Thus, projection is a part of a profile. Preferably, a profile is built for each frame.

An example of a projection is a line-by-line (or column-by-column) agglomeration (e.g. summation) of pixel values with an image frame.

In another embodiment said analysis unit is configured to determine two projection profiles in two predetermined orthogonal directions from said subset of image frames and for determining said amount of direction changes from said projection profiles. This increases the robustness and accuracy of the discrimination between vital sign information and noise.

This can be further improved with an embodiment according to which said evaluation unit is configured to decide that said region of interest of said subset of image frames comprises a vital sign information if direction changes appear at substantially the same moments in time in both projection profiles.

Preferably, a control unit is provided for controlling the number of image frames of said subset of image frames used for determining the amount of direction changes, the predetermined direction change threshold and/or the region of interest within said image frames. Thus, the number image frames can be changed, and subsequent subsets of image frames may also be overlapping and comprise a number of same image frames, i.e. a sliding "window" (corresponding to a subset of image frames) approach may be used in an embodiment.

According to an embodiment said evaluation unit is configured to determine if a number of determined consecutive time distances between direction changes are above a predetermined time distance threshold indicating that said region of interest within said subset of image frames comprises a vital sign information. Also said time distance threshold may be predetermined or changeable, e.g. adaptable according to the number of image frames within the subset or settable by the user.

In an initial step the region of interest shall be selected. For this purpose the device preferably comprises an ROI selection unit for selecting the region of interest within said subset of image frames by determining two projection profiles in two predetermined orthogonal directions from said subset of image frames, dividing said projection profiles into projection areas, determining the amount of direction changes and/or the time distances between direction changes within said projection areas, selecting the two or more adjacent projection areas having the smallest numbers of direction changes and/or the largest time distances between direction changes, said selected projection areas representing the region of interest.

Said ROI selection unit is preferably configured to
select projection areas having an amount of direction changes below a first projection area threshold and/or time distances above a second projection area threshold,
select, among said projection areas, pairs of projection areas in both projection profiles having a substantially equal amount of direction changes and/or substantially equal time distances, said pairs of projection areas defining separate region of interests. Thus, one or more optimal regions of interest can be automatically detected.

While the invention can be used for obtaining various kinds of vital signs, it is preferably suited for obtaining respiratory information, in particular the respiratory rate, of the subject. Accordingly, said processor is preferably configured to determine a respiratory information of the subject from said region of interest within said subset of image frames.

In a preferred embodiment the proposed device further comprises an imaging unit, in particular a camera, for remotely detecting electromagnetic radiation emitted or reflected from the subject. The imaging unit is particularly suited for remote monitoring applications. The imaging unit can comprise one or more imaging elements. For instance, the imaging unit can comprise an array of photodiodes or charge-coupled devices. According to one embodiment, the imaging unit comprises at least two groups of imaging elements each of which is configured for detecting a single one of the data signal components. According to another embodiment, the imaging unit can make use of a single group of imaging elements having a response characteristic allowing for a detection of data signal components. The imaging unit can be further configured for capturing a sequence of image frames alternatingly representing the data signal components.

In another preferred embodiment the proposed device further comprises a radiation source, in particular a light source, for directing electromagnetic radiation to the subject. The radiation source can be embodied by a broadband illumination source and/or can make use of a single group or two or even more groups of radiation elements. However, the proposed device does not necessarily have to comprise radiation source, but can also make use of ambient light sources which are not connected to the device.

According to another aspect of the present invention a device for obtaining a respiratory information of a subject is presented, said device comprising:
an interface that receives image frames of a subject,
an analysis unit that determines the amount of direction changes and/or the time distances between direction changes within a region of interest in a subset of image frames comprising a number of said received image frames, a direction change indicating a change of the direction of motion appearing within said region of interest,
an evaluation unit that determines if said region of interest within said subset of image frames comprises a respiratory information and/or noise by use of the determined amount of direction changes and/or the time distances for said subset of image frames, and
a processor that determines the desired respiratory information of the subject from said region of interest within said subset of image frames if it is determined that said region of interest within said subset of image frames comprises a respiratory information.

Preferably, said respiratory information is the respiration rate of the subject.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
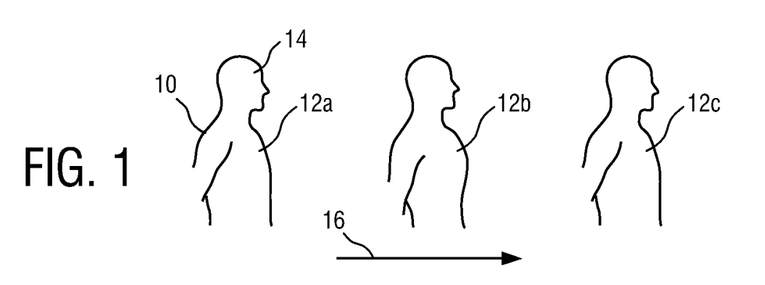
FIG. 1 shows a schematic illustration of an object's motion indicative of an exemplary vital signal.

FIG. 1 shows a schematic illustration of an object 10 which experiences motion indicative of a signal of interest. The object 10 undergoes a characteristic motion of an indicative portion 12 due to respiration. When breathing, expansion and contraction of the lungs causes slight motion of characteristic portions of living beings, e.g. lifting and lowering of the chest. Also abdominal breathing can cause characteristic motion of respective parts of the object's body. At least partially periodic motion patterns induced by physiological processes can occur in many living beings, particularly in humans or animals.

Over time, as indicated by an arrow 16, the indicative portion 12 is moved between a contracted position, indicated by reference numerals 12a, 12c, and an extracted position, indicated by 12b. Essentially, based on this motion pattern, for instance the respiration rate or respiration rate variability can be assessed. While the indicative portion 12 is pulsating over time, a non-indicative portion 14 remains substantially motionless. Certainly, also the non-indicative portion 14 undergoes diverse motion over time. However, these motions do not correspond to the periodic pulsation of the indicative portion 12.

Figure 2:
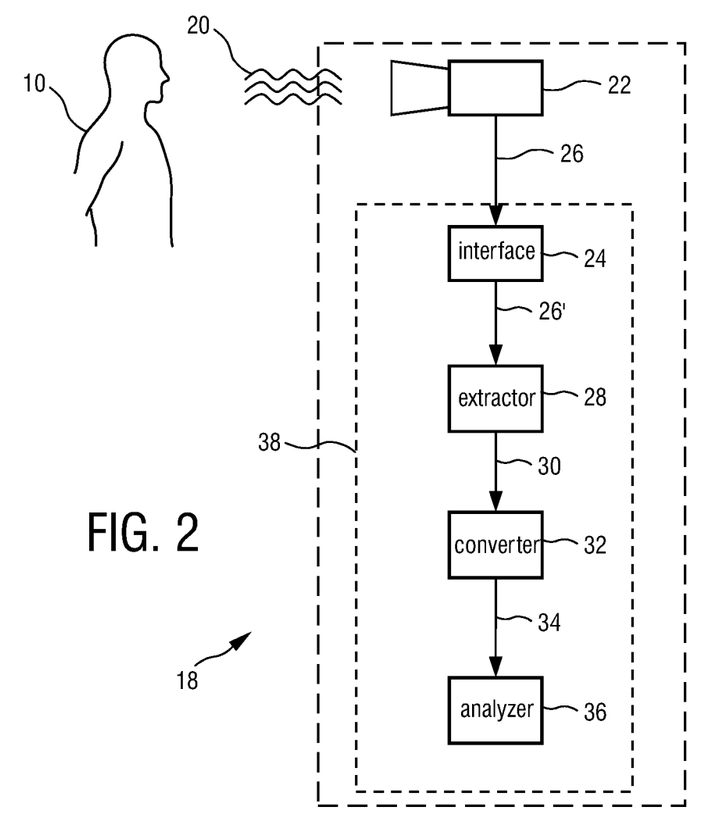
FIG. 2 shows a schematic illustration of a general layout of a known device.

In this context, referring to FIG. 2, a device, as described in WO 2012/140531 A1, for extracting information is illustrated and denoted by a reference numeral 18. The device 18 can be utilized for recording image frames representing the object 10. The image frames can be derived from electromagnetic radiation 20 emitted or reflected by the object 10. For extracting information from the recorded data, e.g. a sequence of image frames, a defined part or portion of the object 10 can be observed by a sensor means 22. The sensor means 22 can be embodied, by way of example, by a camera adapted to capture information belonging to at least a spectral component of the electromagnetic radiation 20. The device 18 also can be adapted to process input signals, namely an input data stream, already recorded in advance and, in the meantime, stored or buffered. As indicated above, the electromagnetic radiation 20 can contain a continuous or discrete characteristic signal which can be highly indicative of at least one at least partially periodic vital signal.

Known methods for obtaining such vital signals comprise tactile respiration rate monitoring or remote respiration rate monitoring relying on markers applied to the object of interest. As indicated above, an alternate approach is directed to unobtrusive remote measuring utilizing image processing methods.

The data stream 26 comprising the continuous or discrete characteristic signal can be delivered from the sensor means 22 to an interface 24. Needless to say, also a buffer means could be interposed between the sensor means 22 and the interface 24. Downstream of the interface 24 an extractor means 28 is provided which is adapted to extract the desired physiological information (namely embedded in the characteristic index elements to be derived therefrom) from a conducted data stream 26' received by the interface 24. Physiological information 30 can be obtained by the extraction, though still comprising disturbing signal components. Further, a converter means 32 may follow which is adapted for processing the physiological information 30 derived by the extractor means 28. The preprocessed signal extracted by the extractor means 28 still can comprise large noise-indicative components. In this connection, the converter means 32 can be applied for isolating and enhancing the desired signal component indicative of the vital signal of interest from the overall signal delivered thereto.

Having extracted a converted signal component 34, further post processing of data can be carried out by an analyzing means 36. To this end, the post processing can comprise clipping, bandwidth filtering and/or Fourier analysis. Further post processing measures can be envisaged contributing to an even further improved detection of the desired signal of interest, e.g. of a dominant respiration rate indicative frequency peak in the continuous or discrete characteristic signal.

The extractor means 28, the converter means 32, and the analyzing means 36 can be jointly embodied by a common processing unit 38, e.g. a central processing unit having a single processor or multiple processors. Also the interface 24 can be connected thereto in a common processing device housing the respective subcomponents. By way of example, the processing device 38 can be embodied by a personal computer driven by respective logic commands. In case the sensor means 22 is also jointly connected to the interface 24 by means of hardware, a capturing unit may house the respective subcomponents. For instance, also a mobile device, e.g. a smart phone, or a mobile health monitoring device, comprising a camera or being connectable to a camera can be utilized for carrying out an embodiment of the invention.

However, in the alternative, it can be envisaged to combine a separate sensor means 22 with the processing device 38. This connection can be established by means of cable links or by means of wireless links. In place of the sensor means 22 also a storage means comprising prerecorded data could be connected to the processing device 28.

Figure 3:
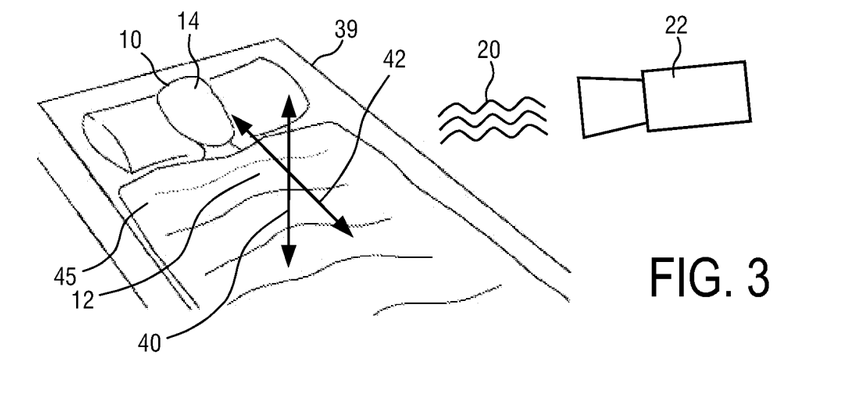
FIG. 3 shows a schematic illustration of an arrangement of an object to be monitored.

With reference to FIG. 3, a common situation in which unobtrusive vital signal detection and monitoring faces major challenges is presented. The object 10, e.g. a patient staying in bed, is resting on a support 39. The object's head comprising the non-indicative portion 14 is exposed and pillowed while the indicative portion 12 is covered by a blanket 45. Thus, the signal caused by motion of the indicative portion 12 is attenuated. Therefore, unobtrusive signal detection is considerably difficult. The sensor means 22 is positioned so as to observe the indicative portion 12. To this end, an exemplary coordinate system represents a direction in which respiration-indicative motion can be expected. This direction is indicated by a disturbance-reduced index element 40. Further, an orthogonal index element 42 (i.e. a direction in which a projection profile can be built) represents a direction in which few or even no respiration-indicative motion can be expected.

Assuming that the desired pulsation is orientated in a single reference direction, it is understood that the orthogonal index element 42 may cover a whole plane orthogonal to the disturbance-reduced index element 40.

Basically, the sensor means 22 can be placed in any direction, provided that the object motion along the disturbance-reduced index element 40 can be sufficiently captured. In this connection, it is preferred if the sensor means 22 is orientated substantially orthogonal to the disturbance-reduced index element 40. However, also significant deviations may occur while the detection of the desired signals is still enabled. In this manner, also considerable object motion, e.g. when tossing and turning in bed, can be accounted for. In fact, placing the sensor means 22 substantially parallel to the disturbance-reduced index element 40 would cause major adverse implications on the signal detection. Again referring to the general arrangement provided in FIG. 3, it is understood that for some potential sensor means orientations it has to be expected that these adverse condition may occur, e.g. when placing the sensor means lateral to the long side of the support 39. Hence, when turning in bed, the reduced index element 40 also turns, thereby reducing the effective angle between the sensor means orientation and the reduced index element 40 leading to a reduced signal level.

In this context, it can be envisaged to arrange two or even more sensor means in distinct positions with respect to the object 10 so as to enable a, so to say, stereometric monitoring capable of tracing all possible orientations of the disturbance-reduced index element 40.

Figure 4:
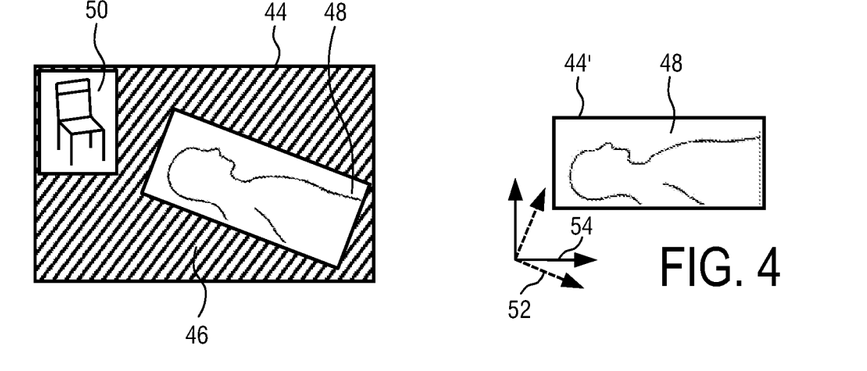
FIG. 4 shows a schematic illustration of an exemplary data stream frame from which a characteristic index element can be derived.

FIG. 4 depicts an exemplary captured image frame 44 showing a representation of the object 10 in an indicative portion 48 of the whole frame. The indicative portion 48 can be detected at this early stage during a pre-processing stage enabling a reduction of the field of view, thereby reducing the data stream volume. To simplify subsequent processing, a coordinate transformation can be applied to the processed image frame 44'. In this way, a deviation between a coordinate system 52 underlying the originally captured image frame 44 and a coordinate system 54 indicative of the disturbance-reduced index element 40 and the orthogonal index element 42 can be compensated for.

Further, FIG. 4 shows a reference portion 50 of the image frame 44. The reference portion may represent steady image objects which can be drawn as reference pattern for motion compensation. Remaining portions 46 of the image frame 44 can be masked and disregarded for subsequent analyses of the data.

Figure 5:
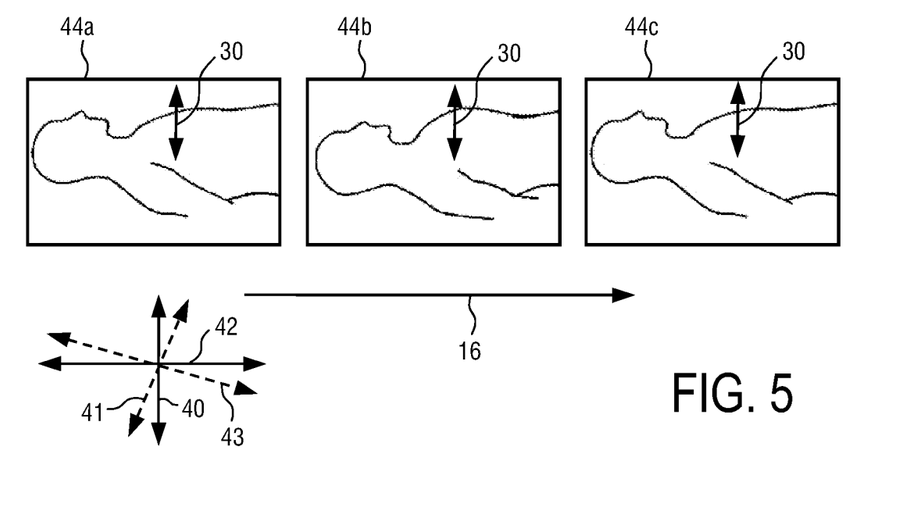
FIG. 5 shows a schematic exemplary data stream frame sequence from which a plurality of characteristic index elements can be derived.

FIG. 5 illustrates a sequence of image frames 44a, 44b, 44c representing the breathing motion of the object 10 already indicated by FIG. 1. The desired vital signal of interest is represented by physiological information indicated by an arrow 30, namely the lifting and lowering of the chest. The physiological information 30 to be extracted is aligned with the disturbance-reduced index element 40. Motion aligned with the orthogonal index element 42 orientated orthogonal to the disturbance-reduced index element 40 is considered to be non-representative of the signal of interest. For the sake of completeness, also a reference motion direction 41 and an orthogonal reference direction 43 are illustrated in FIG. 5. As indicated above, an instant determination of the disturbance-reduced index element 40, e.g. separately for each image frame. may pose major challenges. In this context, it is noted that even a considerable deviation between the disturbance-reduced index element 40 and reference motion direction 41 does not lead to a significant signal loss. Consequently, it is not necessary to precisely determine the disturbance-reduced index element 40 with high precision at all events.

Therefore, small deviations between disturbance-reduced index element 40 and the reference motion direction 41 can be accepted. This enables significant reduction of computing processing requirements. Further, when taking into account the ratio between expected frequencies of the vital signal to be detected and common frame rates utilized for image processing, it is understood that for the determination of the disturbance-reduced index element 40 numerous image frames can be skipped, e.g. merely one out of five or even ten image frames has to be considered. For instance, a control circuit can be established, wherein a threshold is set describing an accepted deviation. In case the threshold is exceeded, the disturbance-reduced index element 40 is adjusted. Finally, a new threshold can be determined.

Figure 6:
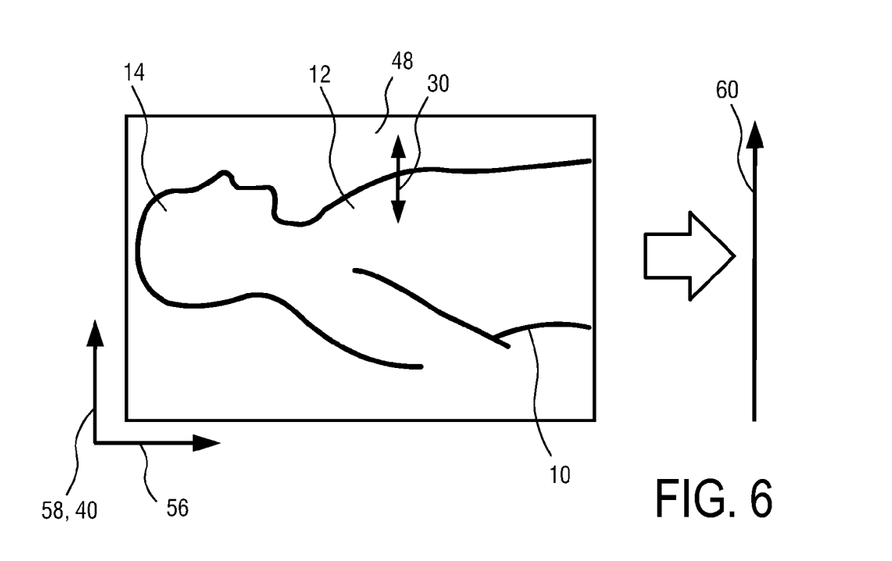
FIG. 6 shows a further schematic exemplary data stream frame and a dimensional reduced characteristic index element derived therefrom.
Figure 7:
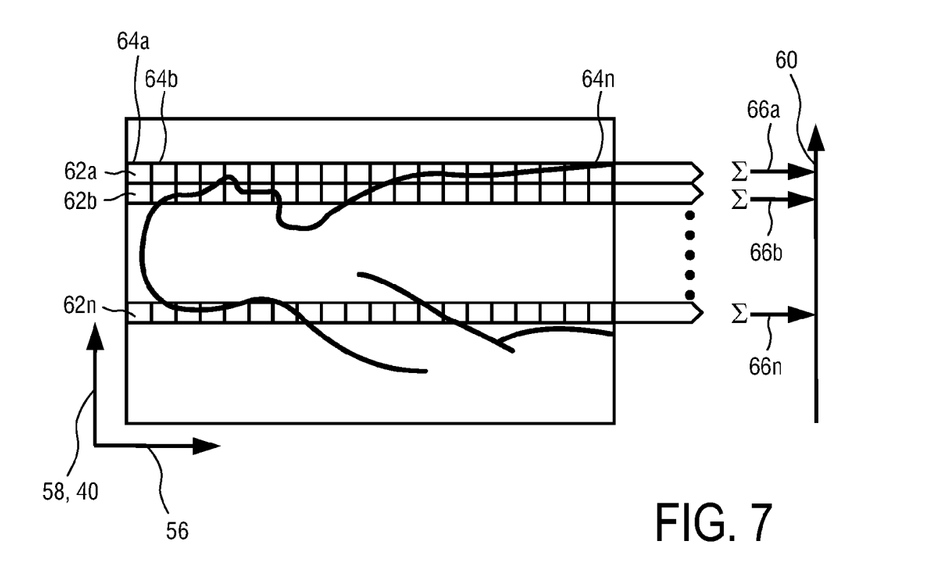
FIG. 7 illustrates an exemplary derivation of the characteristic index element of FIG. 6.

With reference to FIGS. 6 and 7, an exemplary derivation of a characteristic index element 60 representing directional motion information is elucidated. FIG. 6 shows an indicative portion 48 of an image frame. Coordinates describing the position of image entities, e.g. single pixels, are indicated by reference numerals 56, 58, wherein the axis 56 indicates x-coordinates and the axis 58 y-coordinates. Due to a coordinate transformation, ref FIGS. 4 and 5, the disturbance-reduced index element 40 is aligned with the axis 58. When applying a dimension reduction, the goal is to merge image frame properties into a single characteristic index element 60 without significant signal loss in regard of the desired physiological information 30 indicative of the vital signal of interest.

In this context, FIG. 7 describes an agglomeration and projection of sub-entities 62, 64 to the disturbance-reduced index element 40. The sub-entities 62a, 62b, ..., 62n and 64a, 64b, ..., 64n represent respective pixel positions in the image frame. In case the physiological information 30 is fairly represented by motion along the axis 58, a line by line agglomeration of respective pixel values summarizes relevant information of each line in a single entity on the characteristic index element 60. The conversion is indicated by an arrow 66. By way of example, the lines 62a and 62b are supposed to be highly indicative of the desired signal, as the shape of the indicative portion 12, the chest, forms a significant edge undergoing the breathing motion. On the other hand, it can be fairly assumed that the line 62n displaying a back side of the object 10 is less indicative. As outlined above, beside of mere pixel values also further image properties can be drawn for the agglomeration.

Figure 8:
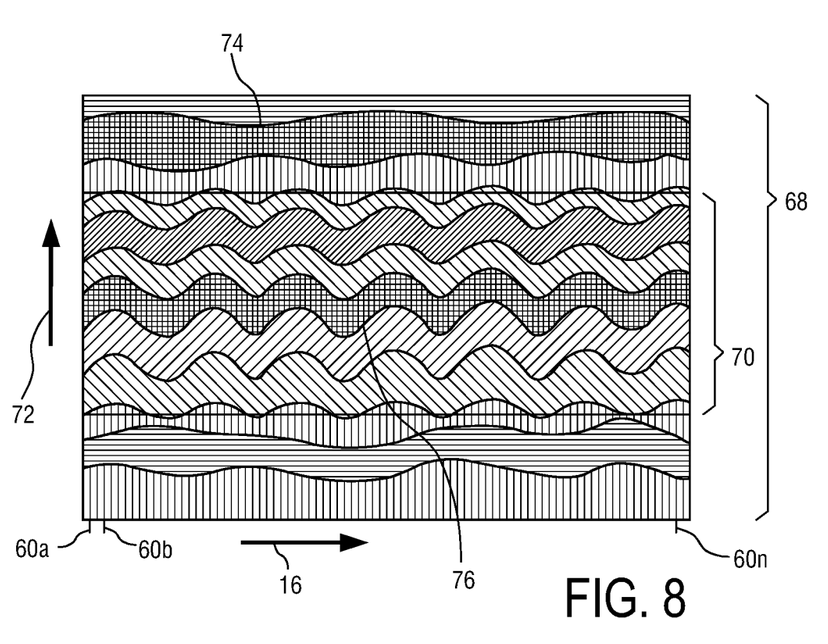
FIG. 8 shows a simplified schematic sequence of characteristic index elements.
Figure 9:
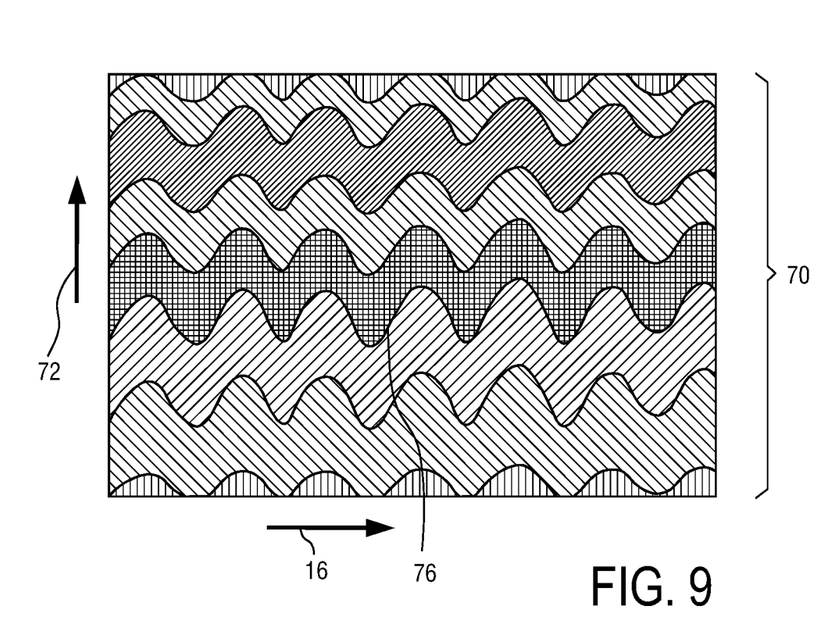
FIG. 9 shows a stretched detail of the simplified schematic sequence of characteristic index elements of FIG. 8.

FIGS. 8 and 9 illustrate an exemplary motion profile obtainable by sequencing a plurality of characteristic index elements 60a, 60b, ..., 60n (representing a sequence of image frames) over time. Integration of discrete elements results in quasi-continuous or continuous wave form. For the sake of visualization, the motion profile shall be understood as represented strictly simplified. Different hatches indicate different line by line agglomeration results. Furthermore, edges provided in the motion profile represent edges rich in contrast in the original image frame (as long as they are substantially orthogonal to the disturbance-reduced index element 40). The temporal pulsation of the edges is understood to be highly-indicative of the desired vital signal.

The general motion profile of FIG. 8 comprises a profile representing the whole continuous or discrete characteristic signal 68 derivable from an image sequence through the dimensional reduction. Furthermore, a subset thereof, a motion-indicative component 70, can be chosen for further analyses. To this end, basic assumptions in regard of the underlying vital signal can be applied. For instance, the motion-indicative component 70 can be supposed to undergo slight periodic motion due to respiration motion of the chest. The frequency of this pulsation can be expected to be within a certain frequency band. In this manner, non-indicative edges 74 can be detected and disregarding during further analyzing steps. On the other hand, indicative edges 76 edges can be drawn or even enhanced for further processing.

An axis 72 indicates the direction of the motion information while the arrow 16 indicates time. It is noted that the axis 72 may comprise qualitative or even quantitative motion information. Generally, nominal position dependent information cannot be drawn from qualitative information, e.g. when a scale representing lengthwise motion is missing. Still, however, frequency information can be extracted from qualitative signals. In this connection, when aiming at quantitative motion detection, it is preferred if also a real object, e.g. a reference scale, allowing a quantitative determination of the motion is monitored, at least during an initial setup.

Generally, the motion profile can be expected to be far more complex showing various fluctuations and numerous variations, both when regarded column by column and line by line. For instance, the motion profile can resemble a spectrum profile undergoing temporal changes. However, no frequency band is shown in this embodiment. Instead, frequency information can be derived from the representation provided in FIGS. 8 and 9.

FIG. 9 illustrates a stretched representation of the motion-indicative component 70 of the motion profile. The indicative edge 76 is enhanced accordingly. In case numerous indicative edges are supposed to be in the motion profile, further correlation measures can be applied so as to improve signal quality. This applies if several edges in the real image undergo motion due to respiration, e.g. a plurality of wrinkles and folds in the blanket covering the object.

The indicative edge 76 can be selected through edge detection measures and further emphasized. Finally, a single wave form highly indicative of the desired signal can be obtained, see also the derivative signal from 86 of FIGS. 11 and 12 in this connection.

Figure 10:
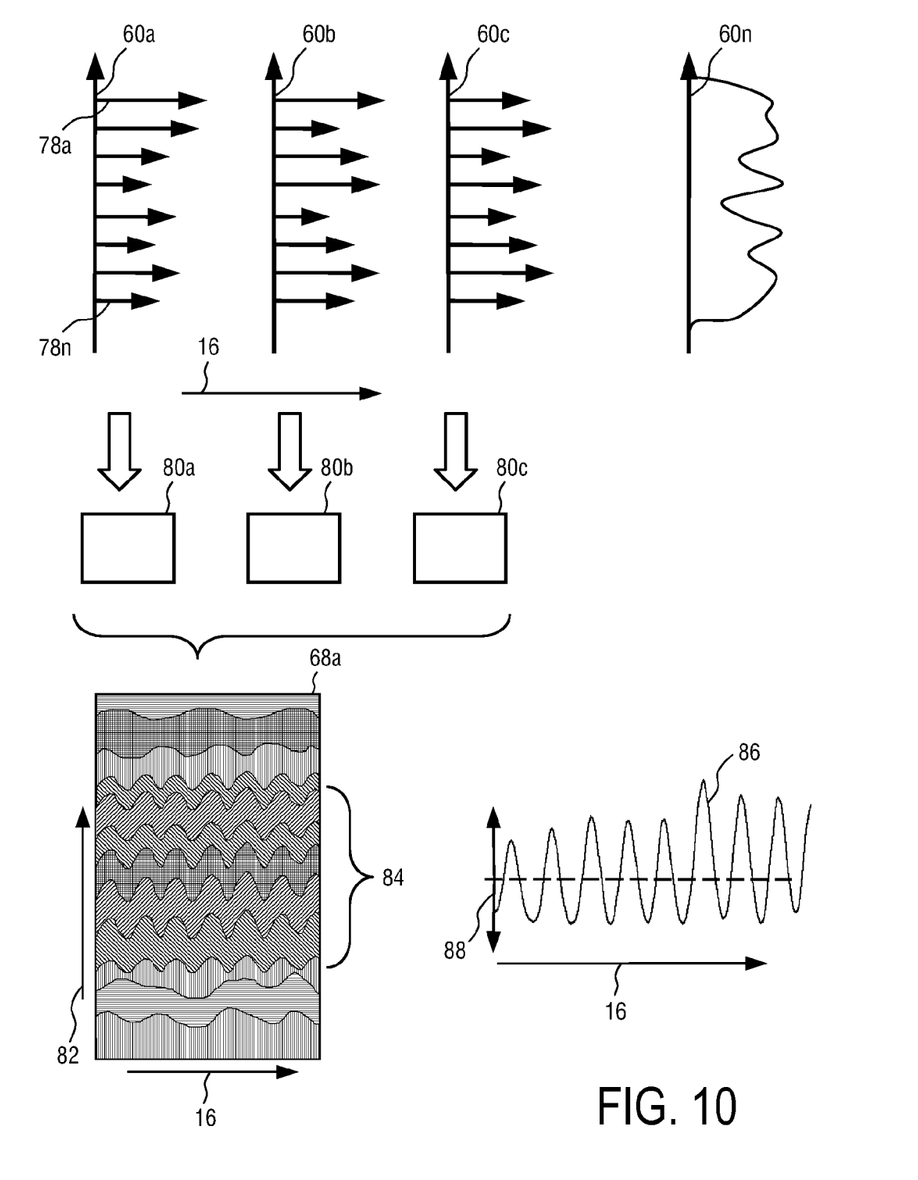
FIG. 10 illustrates a schematic sequence of characteristic index elements to which an integral transformation is applied, and an exemplary illustration of a resulting magnitude range sequence.

In the alternative, referring to FIG. 10, each single characteristic index element 60 can be processed before being sequenced and transferred to the motion profile. In FIG. 10 several consecutive characteristic index elements 60a, 60b, 60c are illustrated, each comprising data stream properties 78a, ..., 78n, each or which representing an agglomerated and projected line of a single image frame, see also FIGS. 6 and 7. Through integration over a plurality of agglomerated data stream properties 78, a characteristic index element 60n can be obtained having a continuous or quasi-continuous wave form.

Further, an integral transformation, especially a Fourier transformation can be applied to each characteristic index element 60a, 60b, 60c, the transformation denoted by 80a, 80b, 80c. Thus, each characteristic index element 60 can be replaced or even supplemented by a magnitude range thereof. In this way, a frequency domain based representation rather that a motion based representation is enabled. The processed signals originating from characteristic index elements can be sequenced over time so as to obtain a magnitude range of interest 84. A magnitude axis 82 indicates the frequencies underlying the representation. Basically, this approach aims at a detection of the desired vital signals based on qualitative wave forms non-indicative of quantitative motion information.

By applying the integral transformation 80, image properties (though captured at the same point in time) are scanned for prominent correlations or frequencies. It could be recognized that also these prominent entities undergo a pulsation over time when the transformed characteristic index elements 60 are being sequenced. Again, applying edge detection measures, a derivative signal form 86 can be obtained highly-indicative of the desired vital signal. The scale 88 of FIG. 10 is considered qualitative in that it is not intended to extract quantitative motion information from the derivative signal form 86 obtained by applying an integral transformation to the characteristic index elements 60. Eventually, whether the characteristic index elements 60 are further processed or not, the highly-indicative derivative signal form 86 can be obtained.

Figure 11:
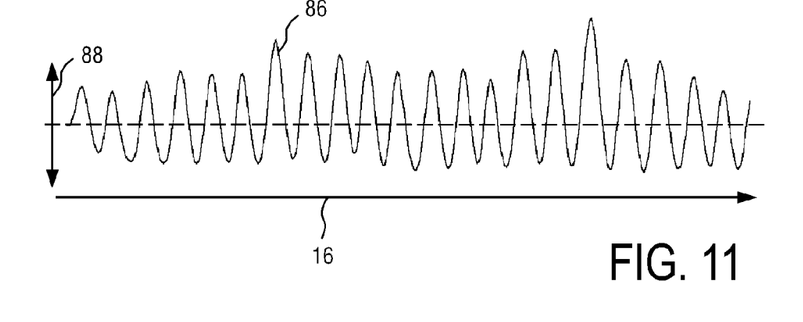
FIG. 11 shows a schematic illustration of derivative signal form.

FIG. 11 shows an illustration of a further exemplary derivative signal form 86. Though the pulsating signal is somehow unsteady in amplitude, the underlying frequency can be obtained by known methods without major efforts. Thus, the desired vital signal, e.g. the respiratory rate of a patient to be monitored, can be extracted from the initial data stream in an unobtrusive manner even under poor ambient conditions.

In case the derivative signal form 86 of FIG. 11 is obtained by sequencing the characteristic index elements 60 without converting motion related signals to frequency band related signals, the scale 88 even can be considered a quantitative scale, either showing absolute or relative position information or, in general, motion information. In this way, even amplitudes, e.g. representing the amount of chest motion, can be detected.

Figure 12:
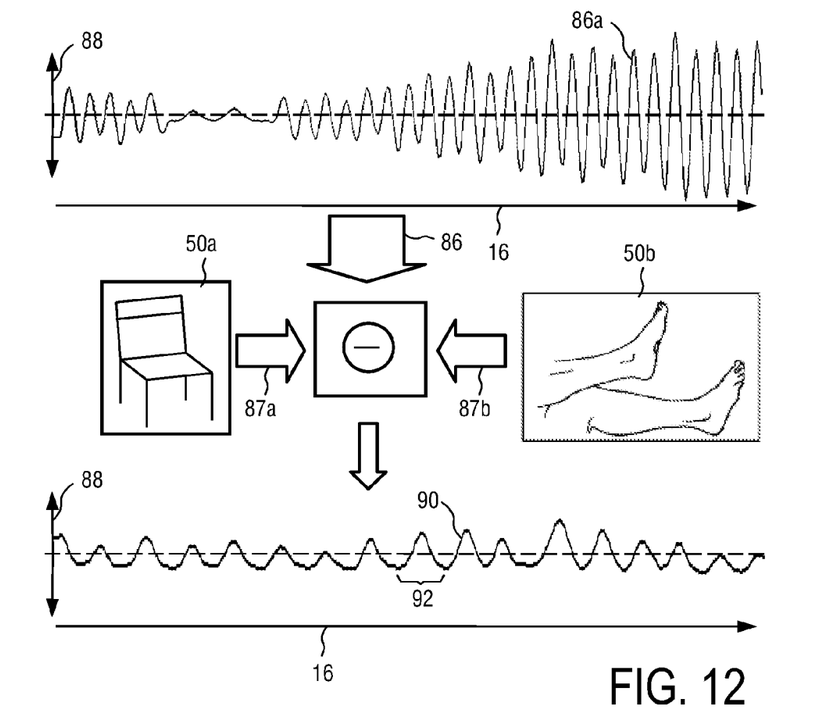
FIG. 12 shows a further schematic illustration of a derivative signal form to which an exemplary compensation for disturbing signal components is applied.

Also FIG. 12 represents an exemplary derivative signal form 86a obtained through data monitoring and processing. In contrast to FIG. 11, the derivative signal form 86a still contains huge remaining disturbing components. This occurs in particular, when the desired object motion is overlaid by considerably disturbing motion, e.g. the object turning in bed, or even global motion of a camera. In that case, a signal decomposition based on reference motion patterns can be envisaged. To this end, reference objects can be monitored in addition to the main objects of interest, see also the reference portion 50 in FIG. 4. Processing reference portion image frames results in reference signals, referred to as remaining disturbing signal components 87. These components can be, so to say, subtracted from the derivative signal form 86a arriving at a genuine motion component 90. In FIG. 12, a global motion indicative remaining disturbing signal component 87a and a disturbing object motion indicative remaining disturbing signal component 87b are considered and illustrated by respective reference portions 50a, 50b. Eventually, the frequency underlying the pulsation of the genuine motion component 90 can be detected, for instance by detecting extreme values thereof, as indicated by reference numeral 92.

As mentioned above the detection of respiration information is based on detecting subtle respiration motion of a body portion of the subject (generally a person, but also an animal) that shows motion caused by respiration, in particular of the chest and/or belly area. The best locations typically contain edge information (for reliable motion estimation) and move due to breathing which typically implies they are connected to the chest or abdominal region (but this can be a blanket covering a neonate, or a shoulder, or a clear detail on the sweater of an adult). Less likely areas are limbs which tend to move independently from the respiratory rate, or parts of the bedding not in mechanical contact with the chest or belly region. However, the known method and device may not sufficiently discriminate desired respiratory signals from noise.

The present invention proposes the simple and low cost device and method to robustly differentiate a noisy signal from shallow respiratory signals for camera-based vital signs monitoring. The proposed device and method proposed here focuses on the raw input values that are used to build the reconstructed signal rather than on the reconstructed signal and observes the amount of direction changes measured per unit of time to discriminate between a signal and absence of a signal. The present invention is based on the observation of these raw input values (i.e. the projections or signals 74, 76 as shown in FIGS. 8 and 9), which revealed that the number of direction (sign) changes in a (noisy) static scene is much higher than when the scene contains breathing motion.

Figure 13:
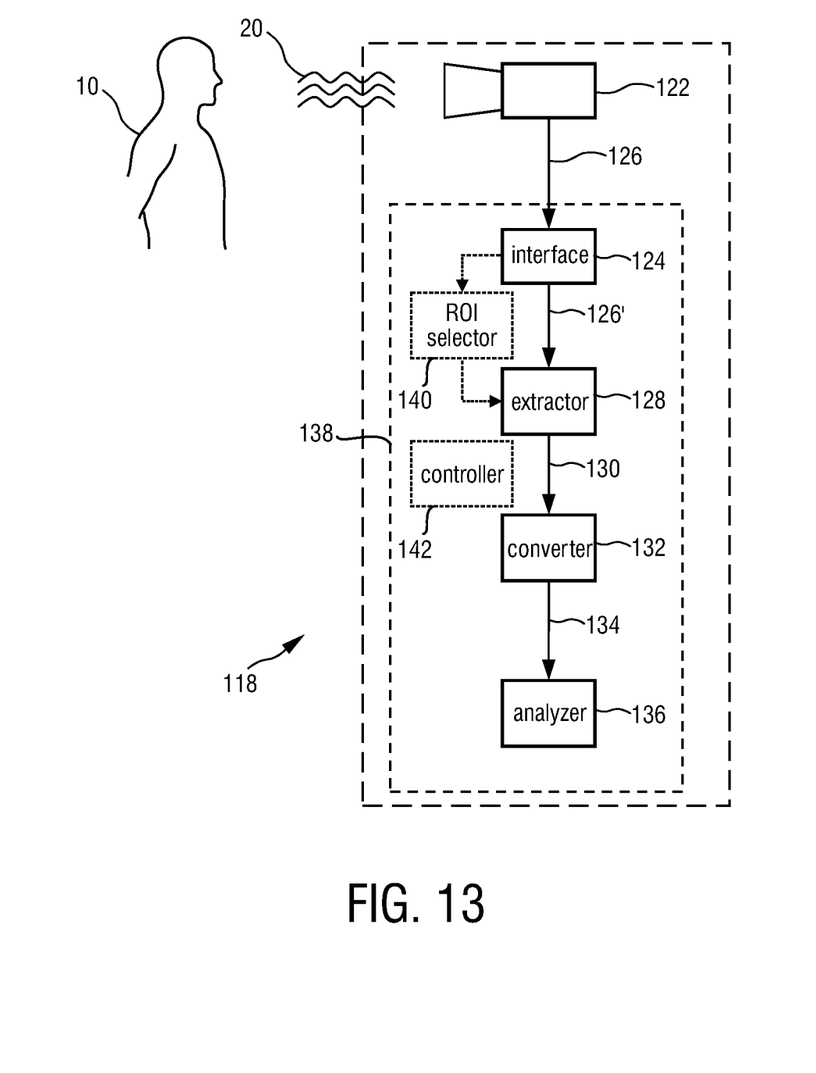
FIG. 13 shows a schematic diagram of a device according to the present invention.

FIG. 13 shows a schematic diagram of an exemplary embodiment of a device 118 for obtaining a vital sign of a subject 10 according to the present invention. This embodiment comprises an imaging unit 122, in particular a camera, for remotely detecting electromagnetic radiation 20 emitted or reflected from the subject 10. An interface 124 is provided for receiving a set of image frames 126 of the subject 10 provided by the imaging unit 122. An analysis unit 128 is provided for determining the amount of direction changes and/or the time distances between direction changes within a region of interest in a subset of image frames comprising a number of image frames of said set 26' of image frames, a direction change indicating a change of the direction of motion appearing within said region of interest. An evaluation unit 132 is provided for determining if said region of interest within said subset of image frames comprises a vital sign information and/or noise by use of the determined amount of direction changes and/or the time distances for said subset of image frames provided as output information 130 from said analysis unit 128. The result 134 of said determination is provided as output from said evaluation unit 132. Finally, a processor 136 is provided for determining the desired vital sign of the subject from said region of interest within said subset of image frames if it is determined that said region of interest within said subset of image frames comprises a vital sign information.

It shall be noted that the imaging unit 122 may also be an external unit not being part of the device, and the set of image frames 126 may also be obtained in advance and stored in a storage unit. Further, the elements 124, 128, 132 and 136 may be implemented by one or more processing units, e.g. a common computer.

Thus, in the proposed camera-based respiration monitoring device, a camera is used to look at the subject to be measured. In particular, the chest/belly area should be in the field of view. Before starting measurement, a region of interest (ROI) is preferably selected in the chest/belly area manually or automatically. For this purpose an optional ROI selection unit 140 is provided, e.g. for selecting the region of interest within said subset of image frames. The subtle respiration motion in the ROI is then continuously measured and analysed to derive the desired vital sign, in particular a respiratory signal.

A direction change thus represents a change of motion direction 72 of an indicative edge 76 for each of projection (=vertical index elements 60a . . . 60n), and the time distance between direction changes thus is the time distance between moments when the motion vector 72 changes its direction for each indicative edge 76 at each projection 60a . . . 60n.

Figure 14:
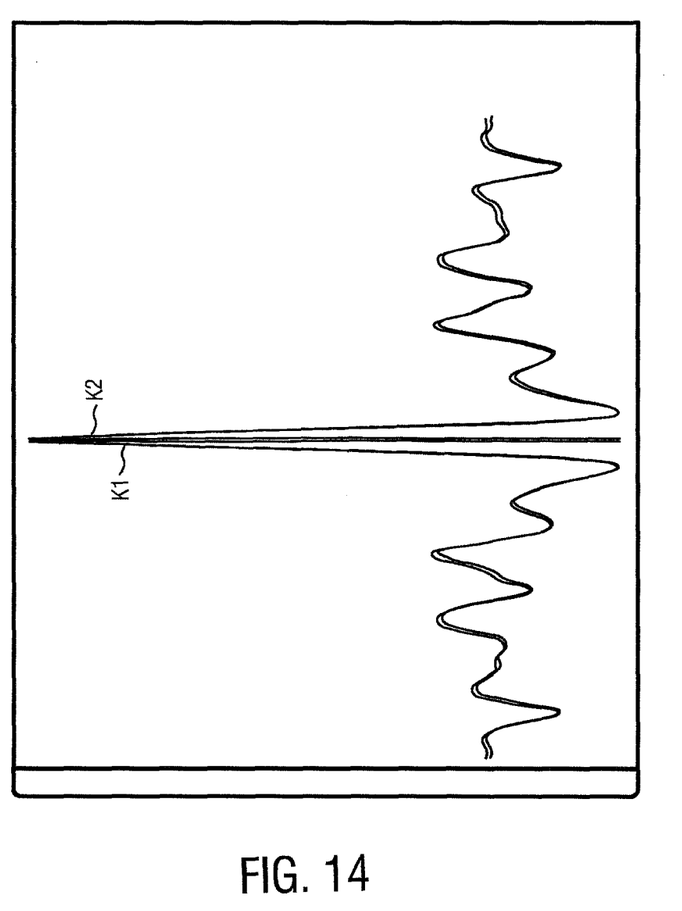
FIG. 14 shows a diagram illustrating the determination of a value from two projection profiles.

FIG. 14 shows a diagram illustrating the calculation of one value from two stored projection profiles. The sign of the projection indicates the direction of the raw signal. In an embodiment the proposed device measures the amount of the observed direction changes in the raw input stream, compares it with a threshold to differentiate between a respiratory signal and noise, and makes a decision, whether a respiratory signal is present.

The two (vertical) curves K1, K2 represent the projections of a video frame at time T and at time T-Δ (typically e.g. 0.2 seconds). The difference (in the vertical direction) of the peaks of these two projections K1, K2 is used to build the respiratory signal (via integration). According to the present invention the number of changes (per unit of time) (and/or the time difference between the changes) of the vertical direction in which the peak moves is observed. For regular breathing (and a decent camera that introduces no compression artifacts) the number of direction changes will be limited. When no breathing activity is present, the noise in the image will also create projection profiles, but they will change direction more often which will be recognized and distinguished from regular breathing according to the present invention.

In a preferred embodiment of the proposed device two parameters are used: the allowed number of direction changes per unit of time (differentiation of shallow breathing from noise) and the time window before making a decision regarding the presence of the respiratory signal (latency for decision making).

In another embodiment of the proposed device the time distance between "zero-crossing" (corresponding to changes of direction) of the raw signal is measured continuously. If the distance between such changes is too short for several consecutive zero-crossings, then it is determined that the breathing signal is absent (e.g. the patient is holding his breath) and the measured signal contains only noise, or the noise signal dominates the extracted respiratory signal, and therefore a reliable measurement of breathing is not possible. The advantage of this embodiment is its very low latency in detection of a "no breathing signal" moment. Thus, in this embodiment the evaluation unit 132 is preferably configured to determine if the determined amount of direction changes is lower than a predetermined direction change threshold indicating that said region of interest within said subset of image frames comprises a vital sign information.

Yet another embodiment of the proposed device makes use of the fact that the respiratory motion of a chest or belly would cause changes of the directions in both horizontal and vertical projections at the same moments of time, while noise, due to its random nature, will results in misaligned changes of direction in horizontal and vertical projections. Hence, in this embodiment said analysis unit 128 is preferably configured to determine two projection profiles in two predetermined orthogonal directions from said subset of image frames and for determining said amount of direction changes from said projection profiles. Preferably, said evaluation unit 132 is configured to decide that said region of interest of said subset of image frames comprises a vital sign information if direction changes appear at substantially the same moments in time in both projection profiles.

The above described embodiments are aiming at detection of an absence of a respiratory signal within a region of interest, which assumes that the ROIs around chest or belly of a person are already (pre-)defined. Considering the example of two ROIs, one ROI (ROI 1) of the chest area providing a respiration signal and another ROI (ROI 2) not containing any part of the person providing noise only. The number of "zero-crossings" or changes of directions in ROI 2 will be much larger, than in ROI 1 (although amplitudes of projections might be similar). In fact, if an image contains only one ROI around chest and/or belly, then only small parts in horizontal and vertical projections (which correspond to ROI) will contain small number of direction changes, while all the rest parts of projections (corresponding to noise) will have large number of direction changes.

This observation is used in further embodiments for fine tuning of the 2D ROI around the chest/belly or even for fully automatic ROI detection. For instance, in an embodiment the following steps are carried out (e.g. by the ROI selection unit 140):

The horizontal and vertical 1D projections are divided into small parts; the lengths of those parts depend on the required granularity of ROI size.

Within each part of both projections, the number of direction changes is calculated.

The adjacent parts with the smallest number of direction changes are selected.

The cross-section of those selected parts of horizontal and vertical projections will represent ROI with respiratory motion.

In the above explained example of two ROIs (ROI 1 and ROI 2) the part of the vertical projection, which corresponds to ROI 2, will have a much larger number of direction changes than the part corresponding to ROI 1.

The above embodiment can be extended further to cover the scenarios when several subjects (monitored patients) are present in the image, and vital signs should be detected and measured for each of present subjects separately. In this case, the above embodiment is extended with the following steps:

Detect all parts in horizontal and vertical projections with number of direction changes below a certain threshold.

Define the pairs of parts in horizontal and vertical projections with equal number of direction changes.

The cross-sections of each of the pairs of parts in horizontal and vertical projections will represent separate ROI around different subject in the scene.

The evaluation unit 132 is configured in an embodiment to decide that said region of interest of said subset of image frames comprises a vital sign information if direction changes appear at substantially the same moments in time in both projection profiles. In another embodiment the evaluation unit 132 is configured to determine if a number of determined consecutive time distances between direction changes are above a predetermined time distance threshold indicating that said region of interest within said subset of image frames comprises a vital sign information.

In still another embodiment the device optionally comprises a control unit 142 for controlling the number of image frames of said subset of image frames used for determining the amount of direction changes, the predetermined direction change threshold and/or the region of interest within said image frames.

Generally, the present invention can be used for deriving different kinds of vital signs. Preferably, said processor 136 is configured to determine a respiratory information of the subject from said region of interest within said subset of image frames.

Further, in an embodiment the device comprises a radiation source, in particular a light source, for directing electromagnetic radiation to the subject, to improve the illumination conditions and to improve the quality of the derived vital sign(s).

By way of example, the present invention can be applied in the field of health care, e.g. unobtrusive remote patient monitoring, neonate monitoring, general surveillances, security monitoring and so-called lifestyle environments, such as fitness equipment, or the like.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for obtaining a vital sign of a subject, comprising:
   an interface configured to receive a set of image frames of a subject,
   one or more processors configured to:
      analyze a subset of image frames of a region of interest in a subject comprising a plurality of contiguous image frames to determine direction changes indicating changes of a direction of motion appearing within said region of interest and at least one of a number of directions per unit time and times between contiguous direction changes,
      determine two projection profiles in two predetermined orthogonal directions from said contiguous subset of image frames and determine the number of direction changes per unit time from said projection profiles,
      decide whether said region of interest of said contiguous subset of image frames comprises vital sign information in response to physical motion direction changes appearing at substantially the same moment in time in both projection profiles,
      extract the vital sign of the subject from said region of interest within said contiguous subset of image frames.

2. A device for obtaining a vital sign of a subject comprising:
   an interface that receives a subset of contiguous image frames of a subject,
   an ROI selection unit that selects a region of interest within said contiguous subset of image frames by:

determining two projection profiles in two predetermined orthogonal directions from said contiguous subset of image frames, dividing said projection profiles into projection areas, determining a frequency of movement direction changes in the contiguous subset and/or times between contiguous direction changes within said projection areas, selecting the two or more adjacent projection areas having a smallest frequency of direction changes and/or largest times between contiguous direction changes, said selected projection areas representing the region of interest;

an evaluation unit that determines if said region of interest within said contiguous subset of image frames comprises vital sign information and/or noise by use of the determined frequency of direction changes and/or the times between contiguous direction changes for said contiguous subset of image frames, and a processor that determines the vital sign of the subject from said region of interest within said contiguous subset of image frames if it is determined that said region of interest within said contiguous subset of image frames comprises vital sign information.

3. The device as claimed in claim 2, wherein said evaluation unit is configured to determine if the determined frequency of direction changes is lower than a predetermined threshold indicating that said region of interest within said contiguous subset of image frames comprises a vital sign information.

4. The device as claimed in claim 2, further comprising a control unit that controls a number of image frames of said subset of image frames used for determining the frequency of direction changes.

5. The device as claimed in claim 2, wherein said evaluation unit is configured to determine if a number of determined consecutive times between direction changes are above a predetermined time threshold indicating that said region of interest within said subset of image frames comprises a vital sign information.

6. The device as claimed in claim 2, wherein said ROI selection unit is further configured to:
select projection areas having the frequency of direction changes below a first threshold and/or times between contiguous direction changes distances above a second threshold,
select, among said projection areas, pairs of projection areas in both projection profiles having a substantially equal frequency of direction changes and/or substantially equal times between direction changes, said pairs of projection areas defining separate region of interests.

7. The device as claimed in claim 2, wherein said processor is further configured to:
determine respiratory information of the subject from said region of interest within said subset of image frames.

8. The device as claimed in claim 2, further comprising:
a camera that remotely detects electromagnetic radiation emitted or reflected from the subject.

9. The device as claimed in claim 8, further comprising:
a light source that directs the electromagnetic radiation to the subject.

10. A method for obtaining a vital sign of a subject, comprising:
receiving a set of image frames of a subject,
determining projection profiles of a contiguous subset in two different directions,
determining a frequency of direction changes and/or times between contiguous direction changes within a region of interest in the projection profiles of the contiguous subset of image frames of said set, a direction change indicating a change of the direction of motion appearing within said region of interest,
determining if said common region of interest within the projection profiles comprises vital sign information and/or noise from the determined frequency of direction changes and/or the times between contiguous direction changes in the projection profiles, and
determining the vital sign from said common region of interest of the projection if said common region of interest within said projection profiles comprises a vital sign information.

11. A computer readable non-transitory medium having instructions stored thereon which, when carried out on a computer, cause the computer to perform the steps of the method as claimed in claim 10.

12. The method as claimed in claim 10, wherein determining whether the common region of interest comprises vital sign information includes determining whether the direction changes appear concurrently in both projection profiles.

13. The method as claimed in claim 10, wherein determining the common region of interest includes:
dividing the projection profiles into projection areas,
determining the frequency of the direction changes and/or the times between contiguous direction changes within the projection areas, and
selecting two or more adjacent projection areas having a smallest frequency of direction changes and/or largest times between contiguous direction changes.

14. A device for obtaining a vital sign of a subject, comprising:
an interface configured to receive a set of image frames of a subject,
one or more processors configured to:
select a common region of interest in the set of image frames,
within a subset of the set of contiguous image frames, determine at least one of a frequency of direction changes and times between contiguous direction changes,
from the direction changes determined in the region of interest, determine whether at least one of the frequency of the direction changes and/or times between contiguous direction changes include vital sign information,
extract a vital sign of the subject from at least one of the frequency of direction changes and the times between contiguous direction changes within the subset of contiguous images; and
a display device configured to display the extracted vital sign.

15. The device as claimed in claim 14, wherein determining whether the determined direction changes includes vital sign information includes:
generating projection profiles in two predetermined direction from the subset of contiguous image frames; and
determining whether the direction changes occur concurrently in both projection profiles.

16. The device as claimed in claim 14, wherein selecting the region of interest in the subset of contiguous image frames includes:
generating two projection profiles in two directions from the subset of contiguous image frames,
dividing each projection profile into projection areas, determining at least one of a frequency of direction changes and times between contiguous direction changes in the projection areas, and selecting common projection areas in the two projection profiles which have at least one of a smallest frequency of direction changes and largest time between contiguous direction changes as the region of interest.

* * * * *